US012616818B2

(12) United States Patent
Choi et al.

(10) Patent No.: US 12,616,818 B2
(45) Date of Patent: May 5, 2026

(54) MAGNETIC ACTUATION SYSTEM COMPATIBLE WITH C-ARM

(71) Applicant: MIRACURE Co., Ltd, Goyang-si (KR)

(72) Inventors: Hong Soo Choi, Daegu (KR); Hak Joon Lee, Daegu (KR); Jin Young Kim, Daegu (KR)

(73) Assignee: MIRACURE Co., Ltd, Goyang-si (KR)

( * ) Notice: Subject to any disclaimer, the term of this patent is extended or adjusted under 35 U.S.C. 154(b) by 257 days.

(21) Appl. No.: 18/494,369

(22) Filed: Oct. 25, 2023

(65) Prior Publication Data

US 2024/0139474 A1 May 2, 2024

(30) Foreign Application Priority Data

Oct. 26, 2022 (KR) ........................ 10-2022-0138815

(51) Int. Cl.
| | |
|---|---|
| *A61M 25/01* | (2006.01) |
| *A61B 6/00* | (2024.01) |
| *A61B 34/00* | (2016.01) |

(52) U.S. Cl.
CPC ....... *A61M 25/0127* (2013.01); *A61B 6/4441* (2013.01); *A61B 6/487* (2013.01); *A61B 34/73* (2016.02); *A61B 2034/731* (2016.02)

(58) Field of Classification Search
CPC ......... A61B 6/487; A61B 34/73; A61B 34/72; A61B 6/4441; A61B 2090/3764; A61B 2034/731; A61B 2034/732; A61B 90/36; A61B 5/05; A61B 5/062; A61B 34/20; A61B 6/547; A61B 5/06; A61B 2034/2051; A61B 8/00; A61B 5/055; A61B 2090/376; A61B 34/10; A61B 50/13; A61B 34/32; A61B 2034/303; A61B 8/4411; A61B 8/4455; A61B 10/00; A61B 8/4281;
(Continued)

(56) References Cited

U.S. PATENT DOCUMENTS

| | | | |
|---|---|---|---|
| 2002/0022777 A1* | 2/2002 | Crieghton, IV ....... | A61B 34/73 600/407 |
| 2005/0169510 A1* | 8/2005 | Zuhars .................. | A61B 6/466 382/131 |

(Continued)

FOREIGN PATENT DOCUMENTS

| | | |
|---|---|---|
| CA | 2 542 863 A1 | 5/2005 |
| KR | 10-1740553 B1 | 5/2017 |

(Continued)

OTHER PUBLICATIONS

Extended European Search Report dated Mar. 15, 2024 in App. No. 23205640.8.
(Continued)

*Primary Examiner* — Irakli Kiknadze
(74) *Attorney, Agent, or Firm* — NSIP Law

(57) ABSTRACT

Provided is a magnetic actuation system controlling a magnetic microrobot, a magnetic actuation catheter, or a guide wire by using a magnetic field, and more particularly, a magnetic actuation system compatible with a C-arm that is applied to the C-arm, which is a mobile X-ray fluoroscopy device, in order to enable control of the microrobot or a catheter treatment in a human body by using the C-arm.

20 Claims, 19 Drawing Sheets

(58) Field of Classification Search
CPC .......... A61B 2017/3413; A61B 8/4472; A61B
17/3403; A61B 8/4422; A61B 5/287;
A61B 5/283; A61B 5/6852; A61B 46/00;
A61B 5/742; A61B 8/467; A61B 8/463;
A61B 8/0841; A61B 46/10; A61B 90/40;
A61B 8/0833; A61B 2090/372; A61B
2560/0276; A61B 8/0891; A61B
2090/3954; A61B 2090/378; A61B 34/25;
A61B 5/7475; A61B 5/743; A61B 90/37;
A61B 90/98; A61B 2090/374; A61B
90/10; A61B 1/00158; A61B 2034/733;
A61B 2034/102; A61B 17/3207; A61B
2017/00252; A61B 2034/2072; A61B
2034/256; A61B 2034/2055; A61B
2034/2068; A61B 2090/3958; A61M
25/0127; A61M 25/104; A61N 2/06;
A61N 2/00; A61N 2/02; A61F 9/0008;
A61K 41/00; H02K 41/00; G06F
19/3481; G16H 50/50
USPC ...................................... 378/62; 382/131, 132
See application file for complete search history.

(56)                References Cited

U.S. PATENT DOCUMENTS

| | | |
|---|---|---|
| 2008/0204012 A1 | 8/2008 | Krueger et al. |
| 2022/0249186 A1* | 8/2022 | Jang .......................... H01F 7/20 |

FOREIGN PATENT DOCUMENTS

| | | |
|---|---|---|
| KR | 10-2289065 B1 | 8/2021 |
| KR | 10-2022-0004420 A | 1/2022 |
| KR | 10-2379538 B1 | 3/2022 |
| KR | 10-2389251 B1 | 4/2022 |
| KR | 10-2022-0072075 A | 6/2022 |
| KR | 10-2436113 B1 | 8/2022 |
| WO | 2018/030610 A2 | 2/2018 |
| WO | 2018/030610 A3 | 2/2018 |

OTHER PUBLICATIONS

Korean Office Action dated Aug. 30, 2024 in Application No.
10-2022-0138815.

* cited by examiner

[FIG. 1]
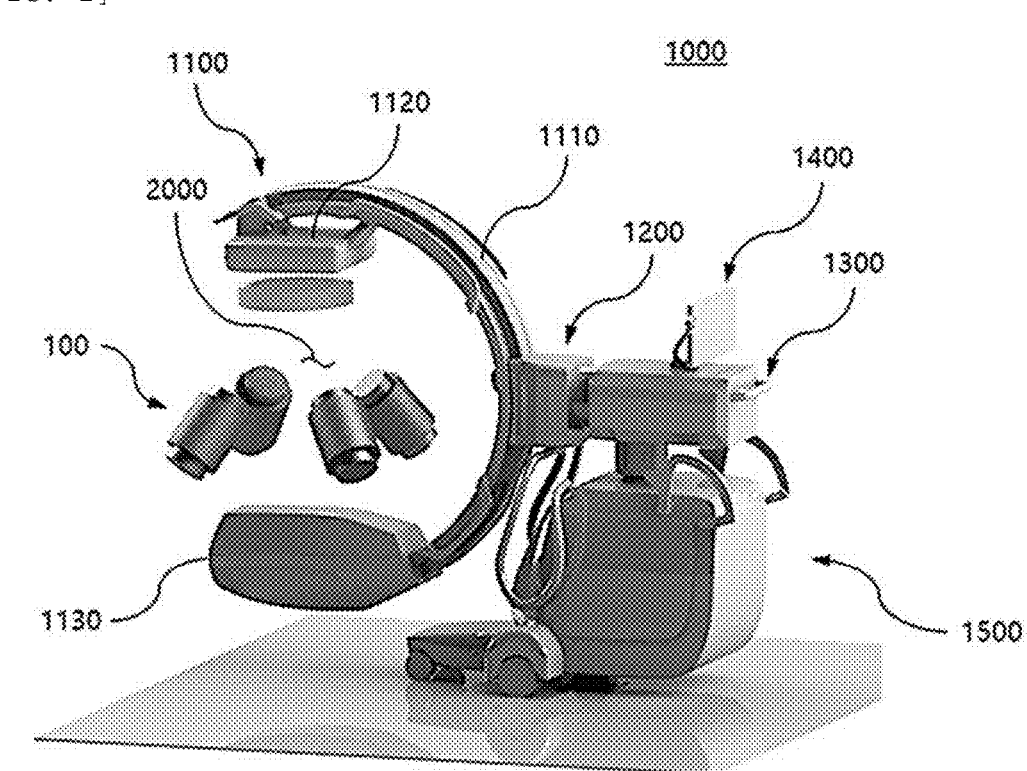

[FIG. 2]
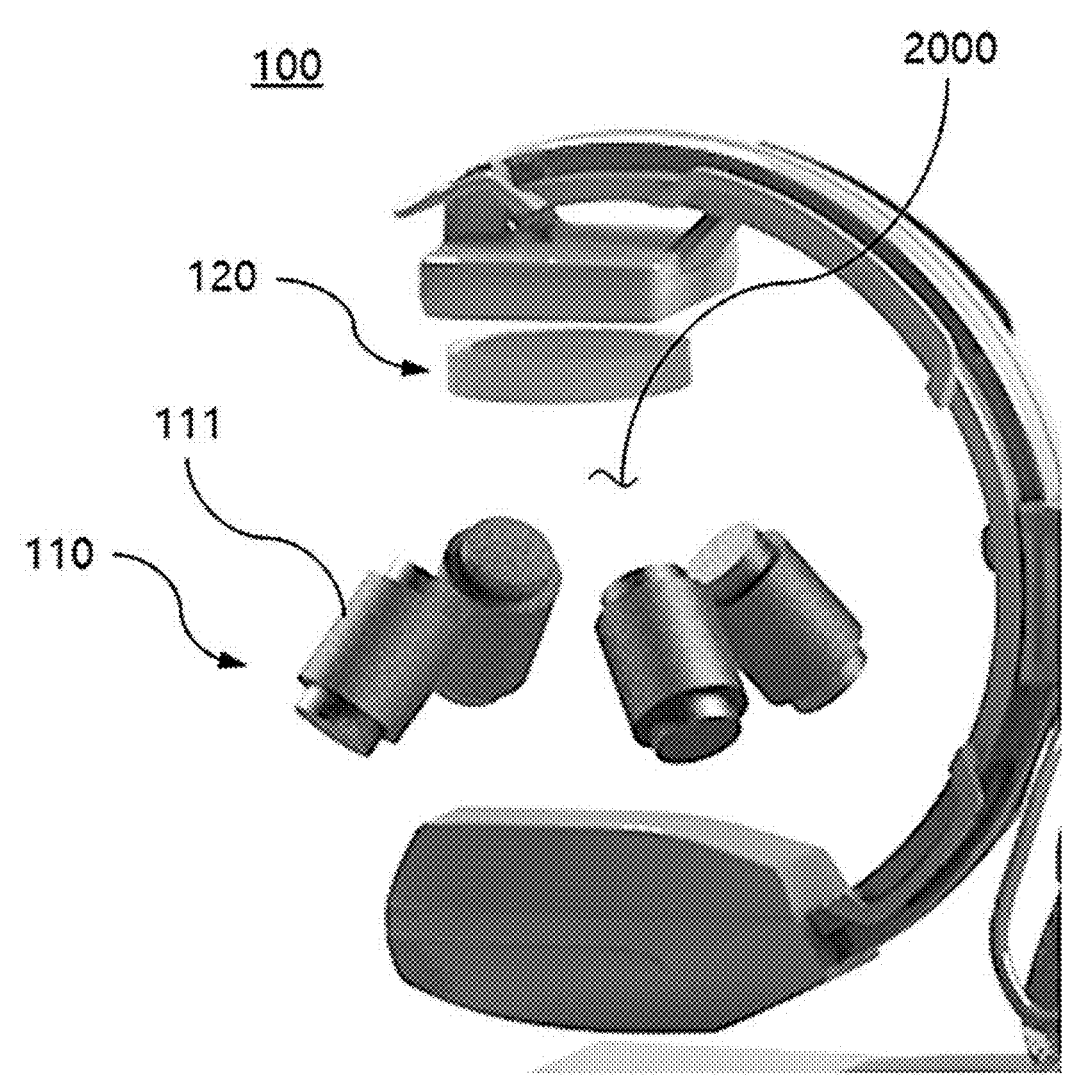

[FIG. 3]
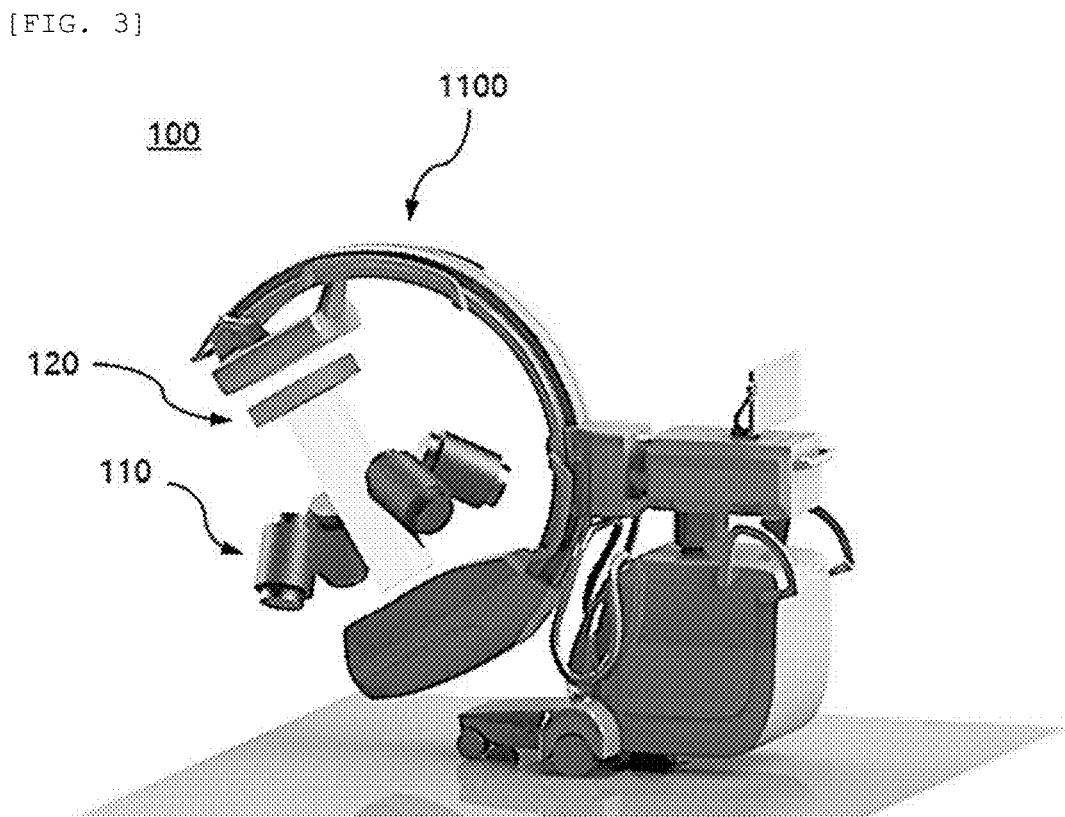

[FIG. 4]
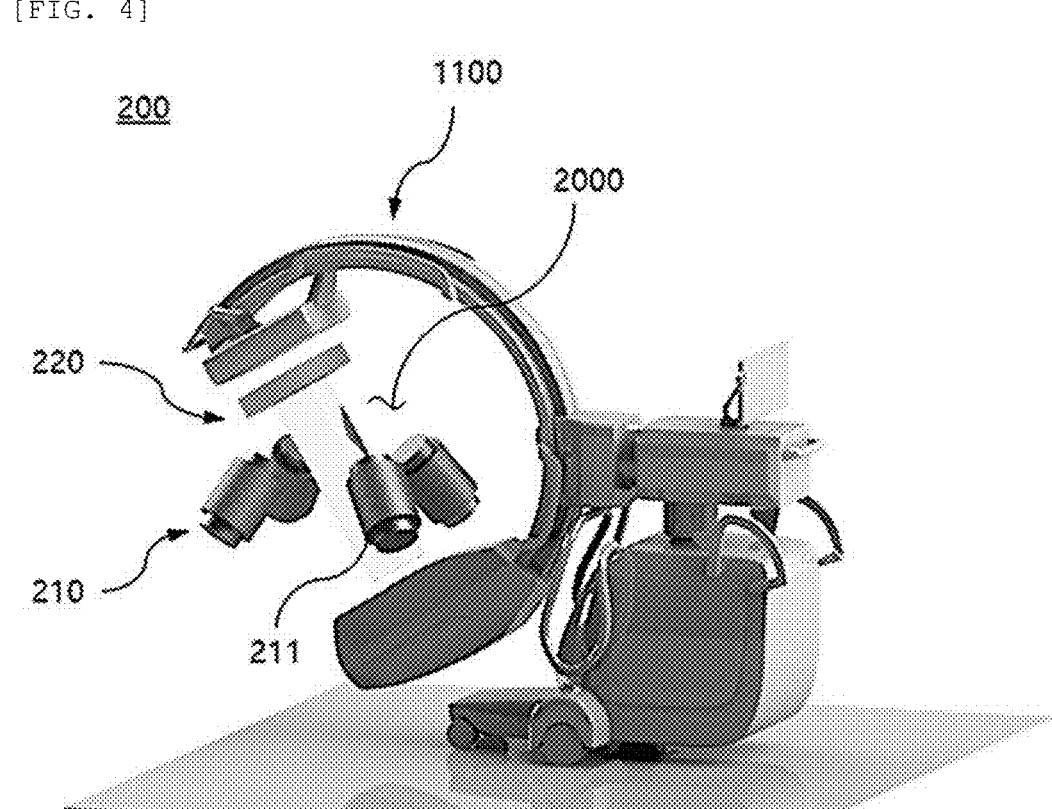

[FIG. 5]
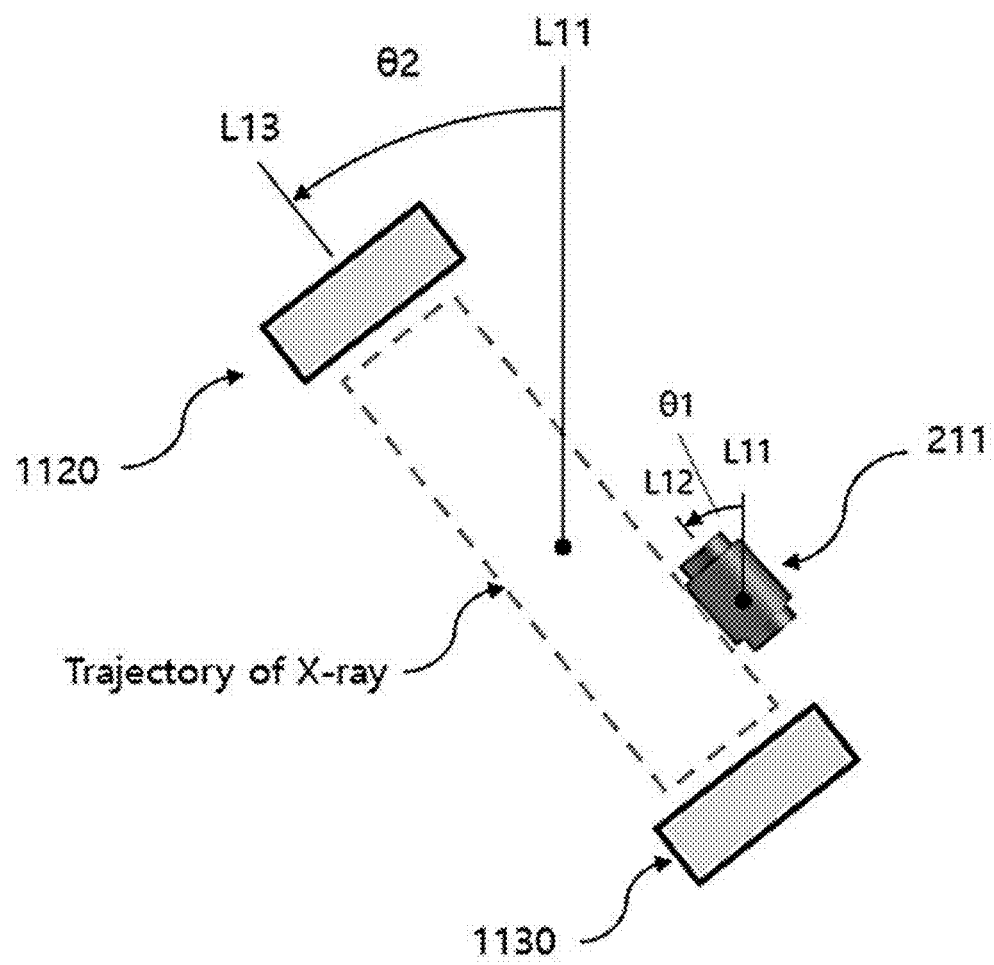

[FIG. 6A]
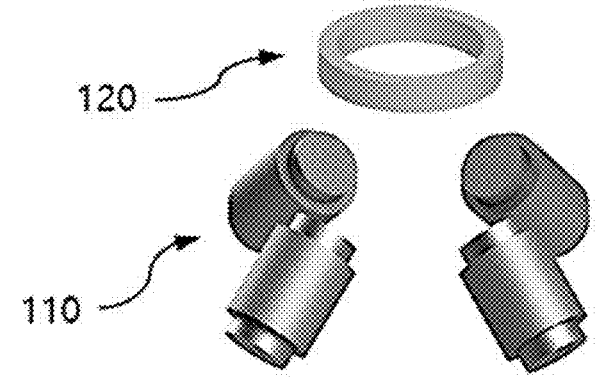
[FIG. 6B]
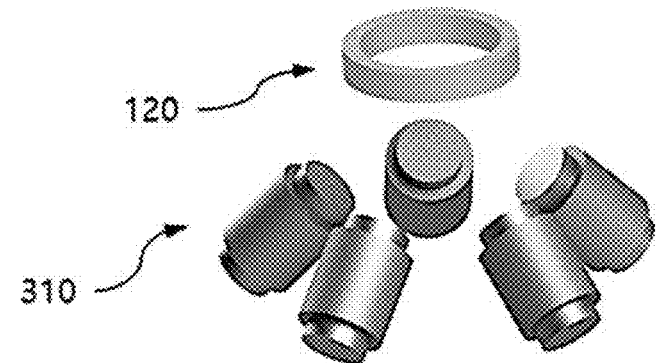

[FIG. 6C]
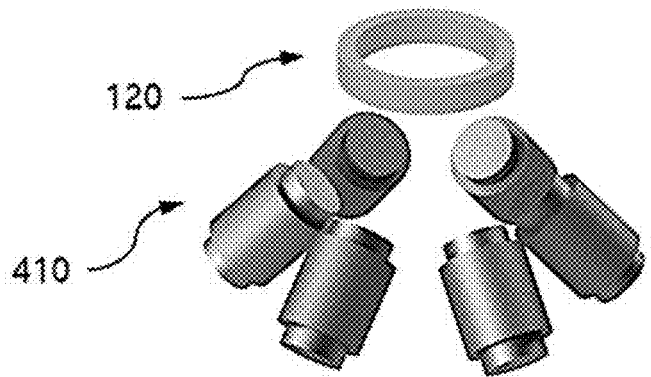

[FIG. 7A]
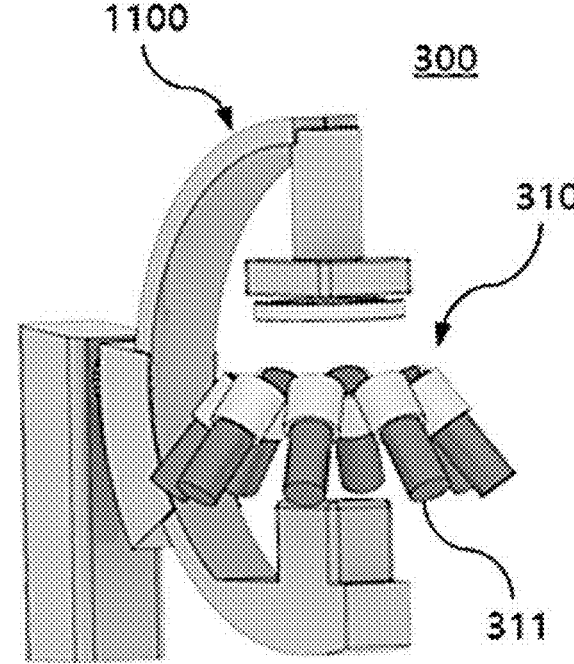
[FIG. 7B]
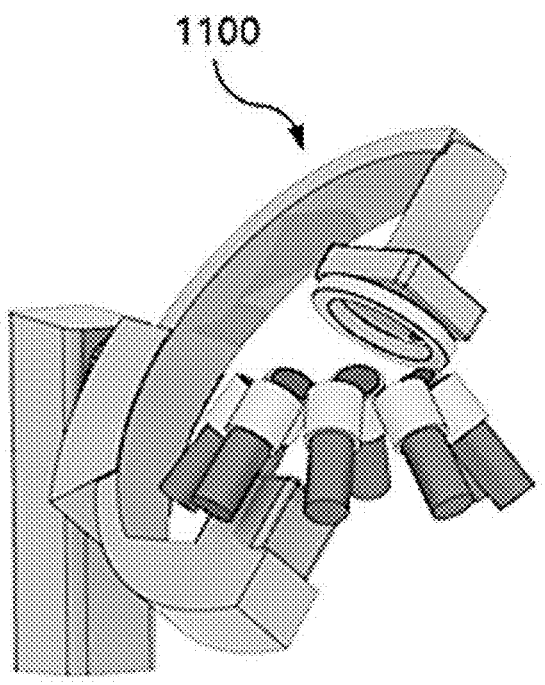

[FIG. 7C]
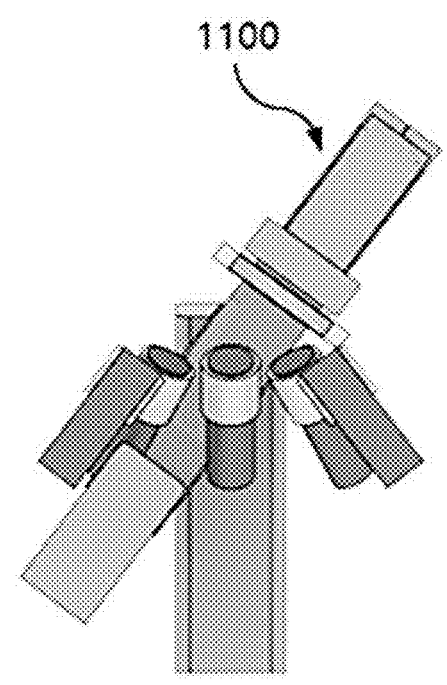
1100

[FIG. 8A]
DIRECTION IN WHICH
ELECTROMAGNET IS
ROTATABLE AT MAXIMUM ANGLE
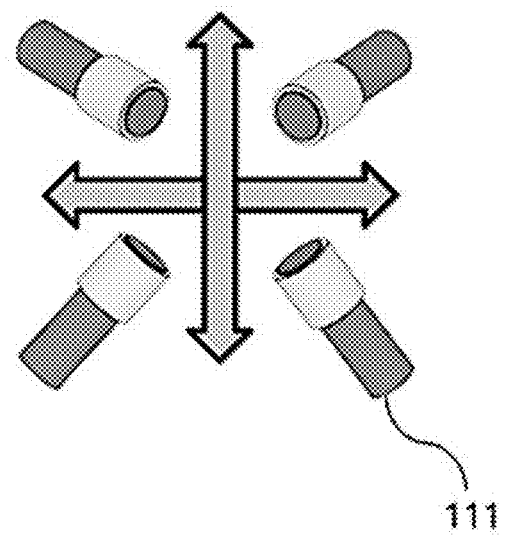
111
[FIG. 8B]
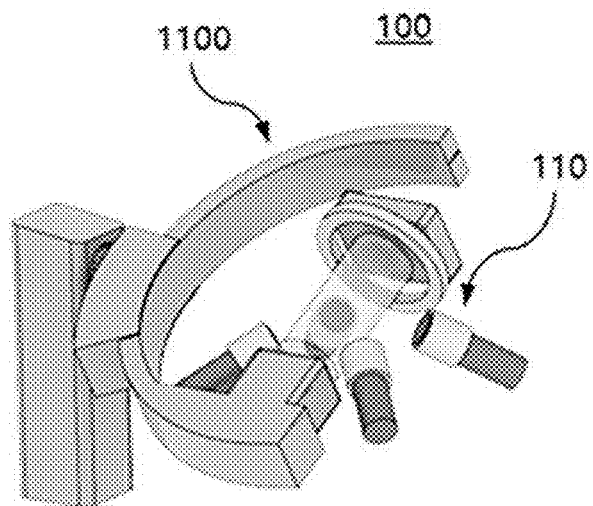
1100     100     110
ROTATED IN
X-AXIS DIRECTION

[FIG. 8C]
1100
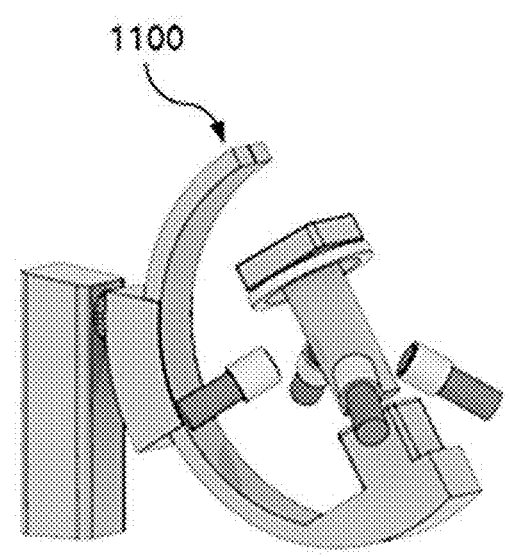
ROTATED IN
Y-AXIS DIRECTION

[FIG. 9A]
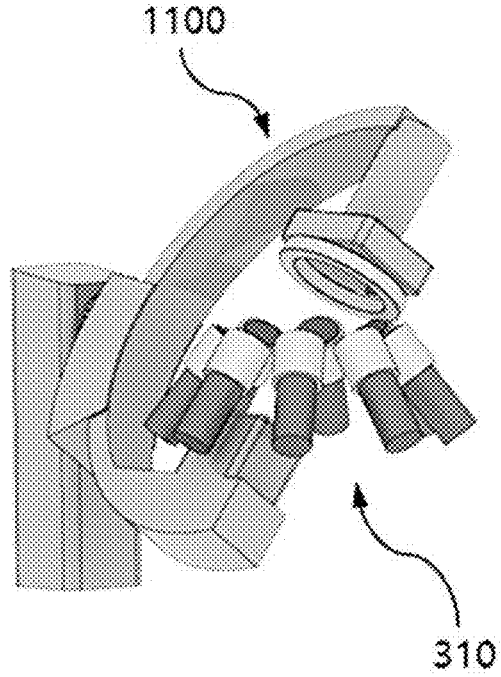
[FIG. 9B]
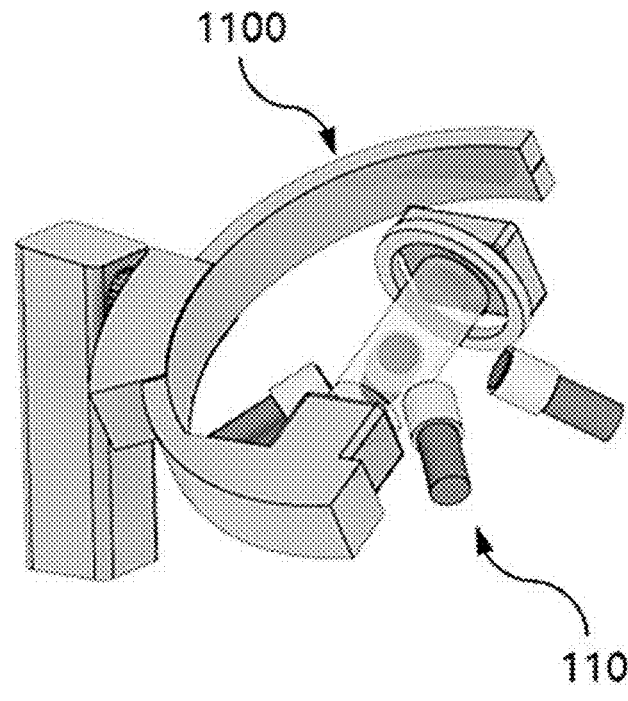

[FIG. 10]
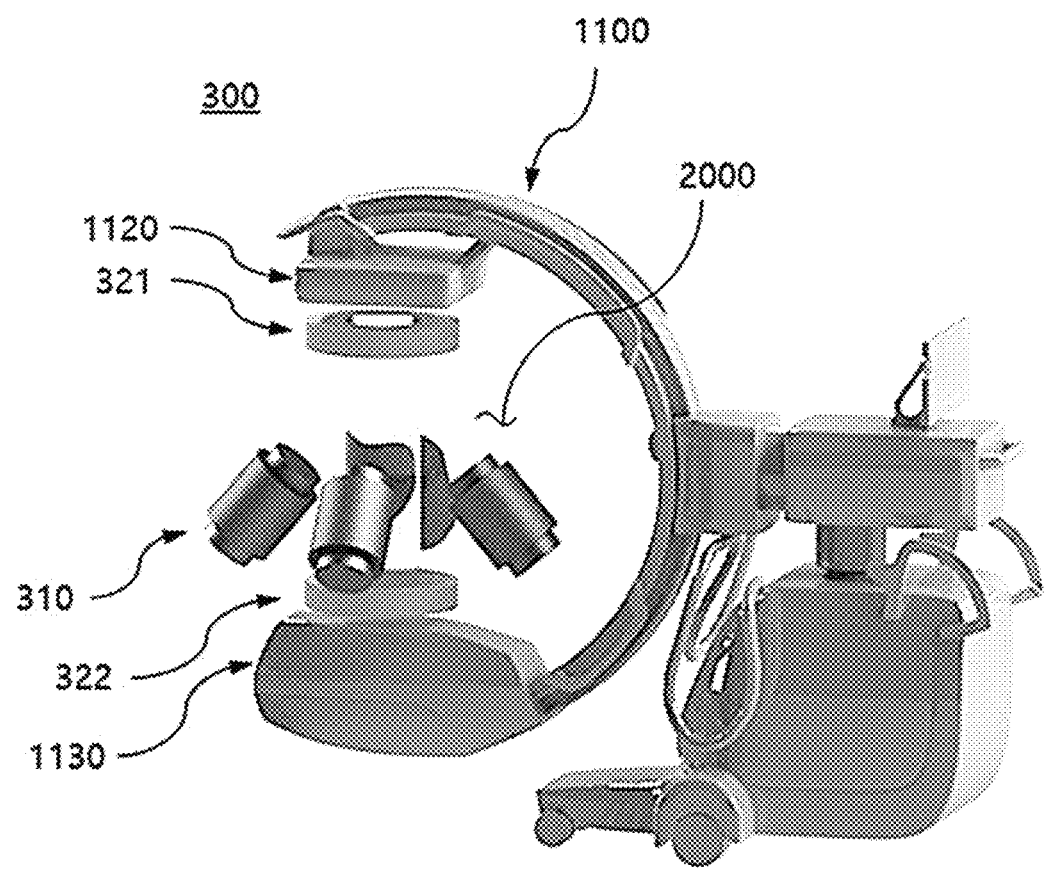

[FIG. 11A]
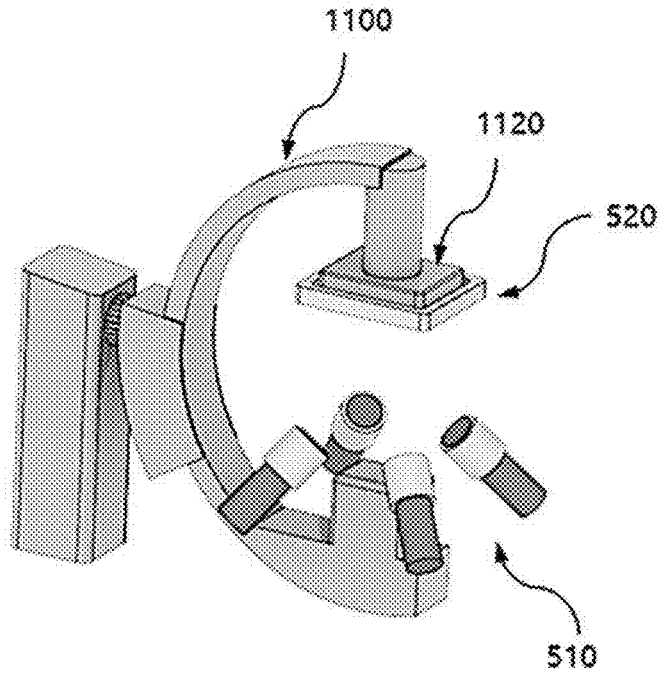
[FIG. 11B]
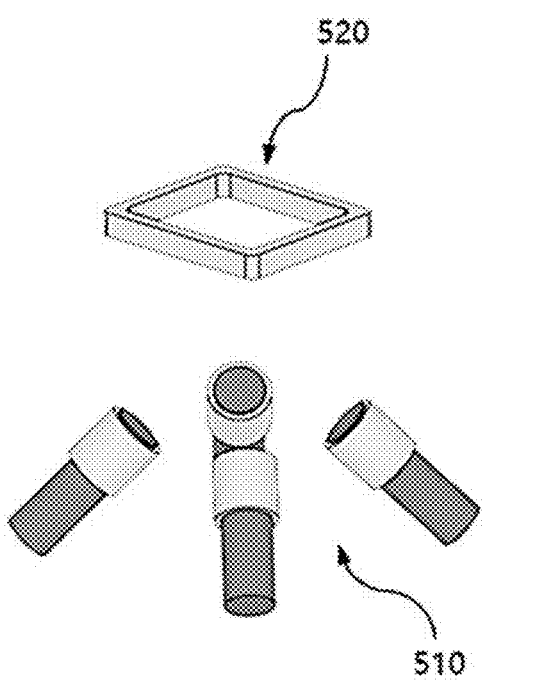

[FIG. 12]
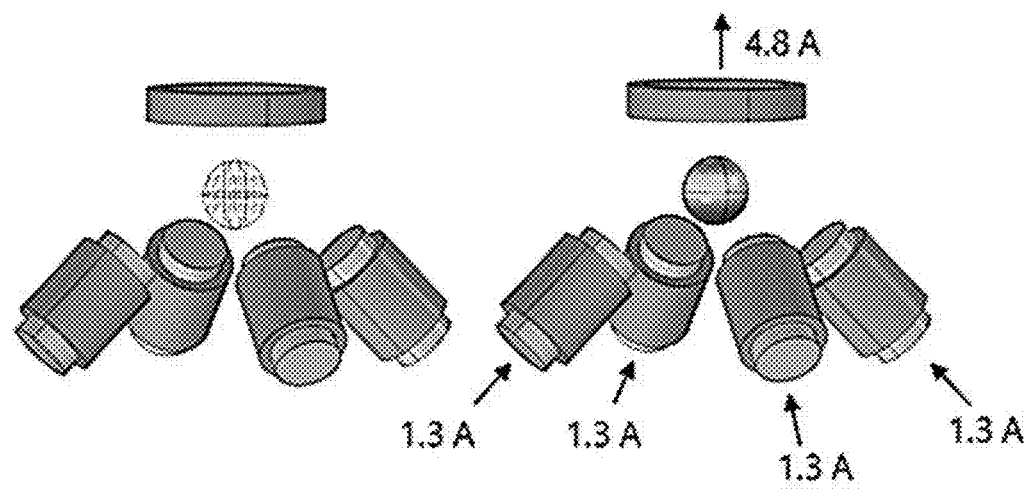
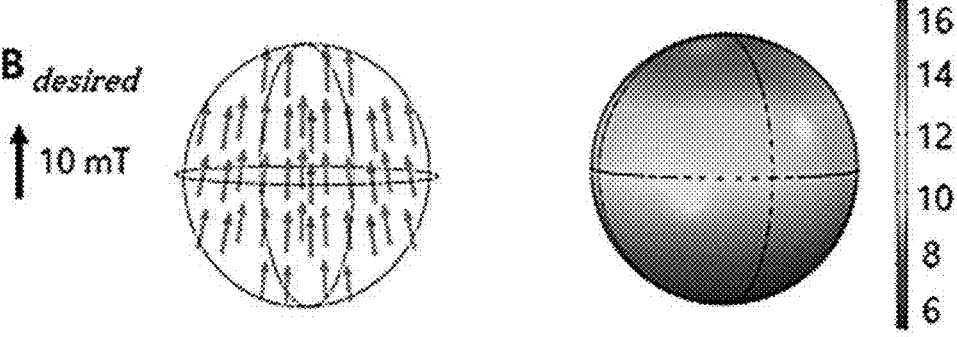

[FIG. 13]
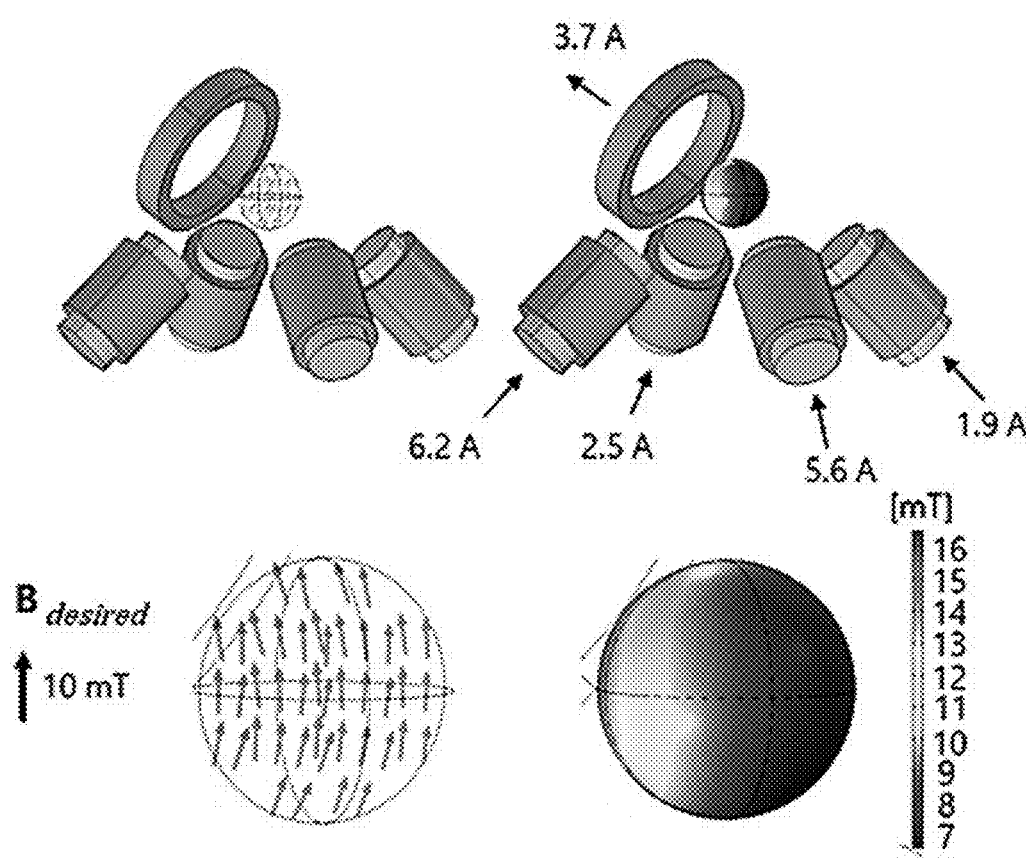

[FIG. 14]
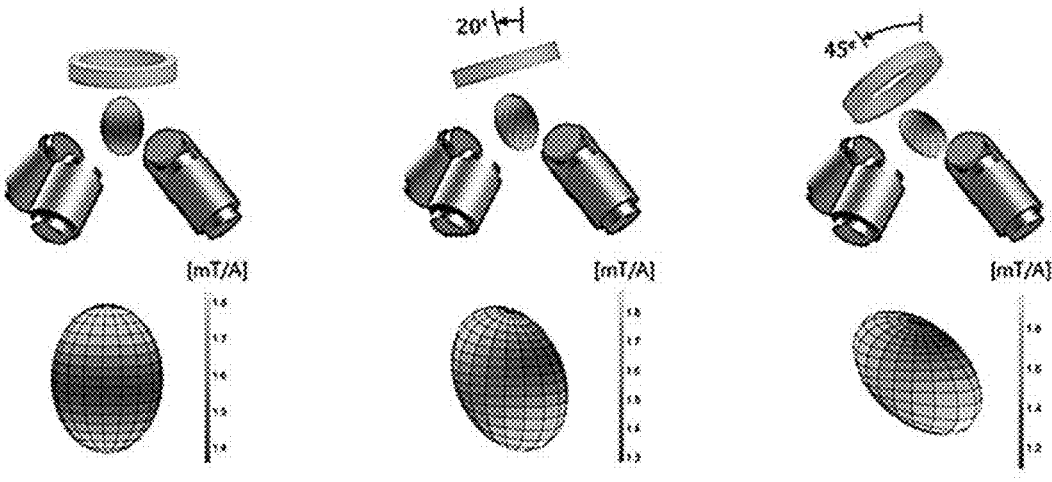
[FIG. 15]
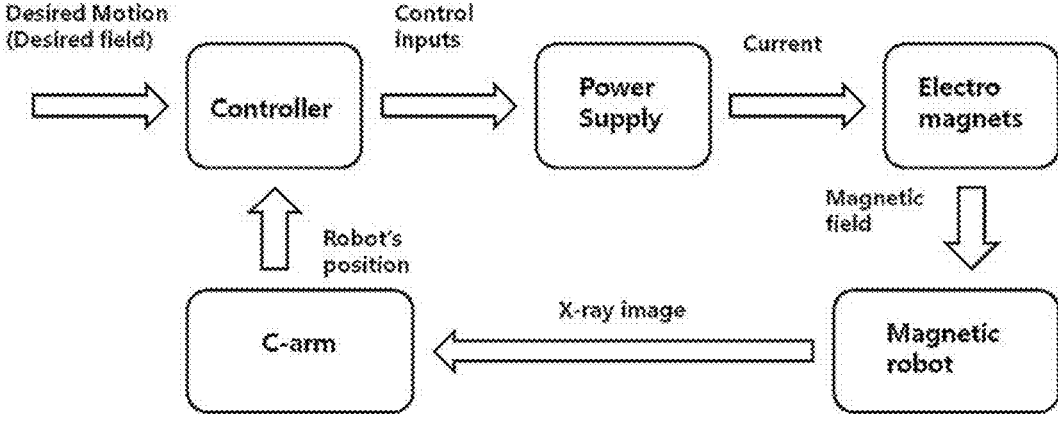

[FIG. 16]
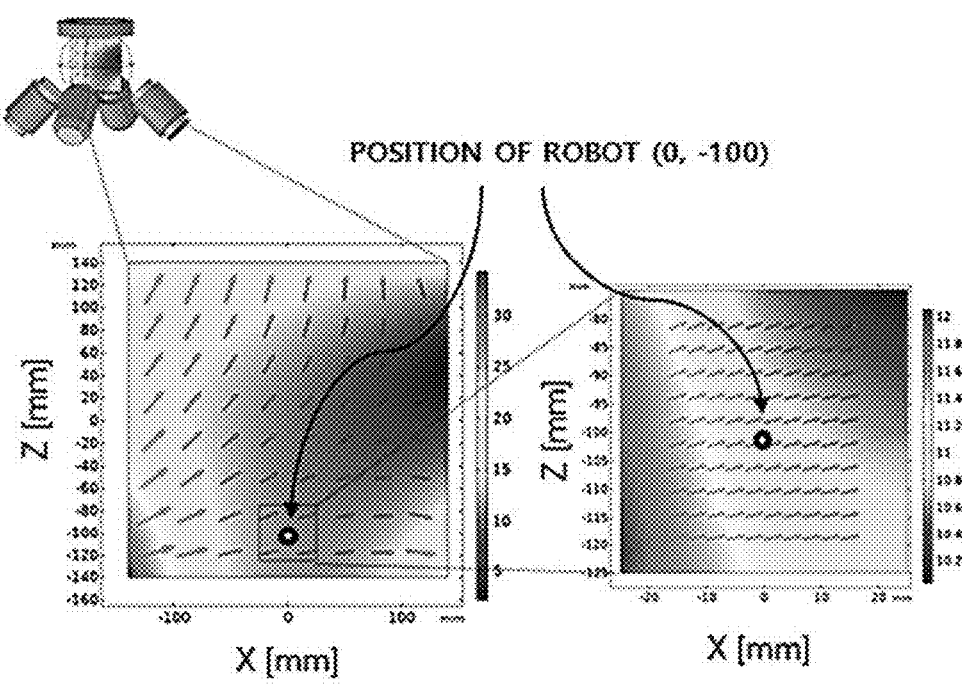
POSITION OF ROBOT (0, -100)
CONTROL MAGNETIC FIELD
WHEN THERE IS NO POSITION INFORMATION OF ROBOT

[FIG. 17]
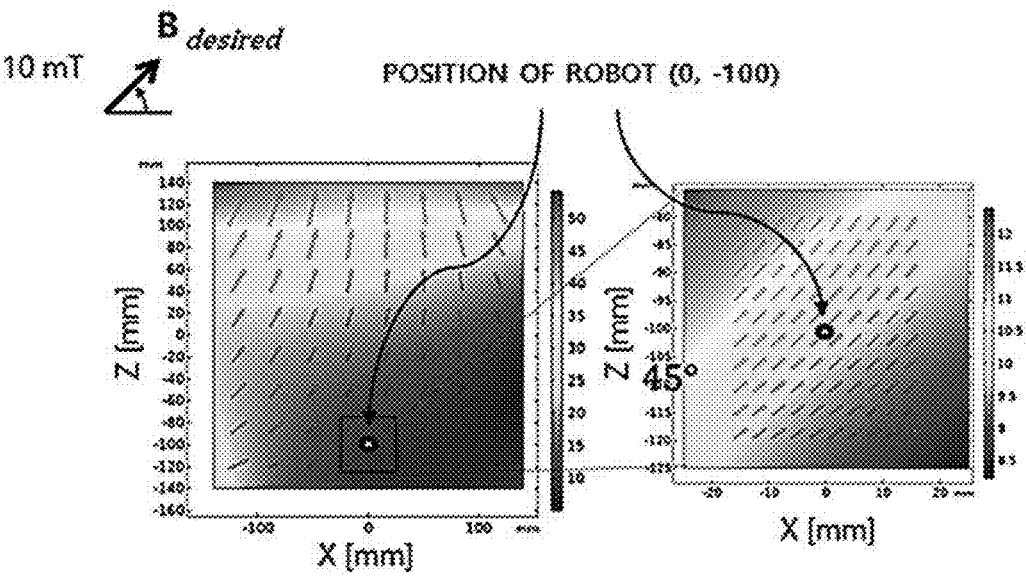
CONTROL MAGNETIC FIELD
BY USING POSITION INFORMATION OF ROBOT

MAGNETIC ACTUATION SYSTEM COMPATIBLE WITH C-ARM

CROSS-REFERENCE TO RELATED APPLICATIONS

This application claims priority under 35 U.S.C. § 119 to Korean Patent Application No. 10-2022-0138815, filed on Oct. 26, 2022, in the Korean Intellectual Property Office, the disclosure of which is incorporated herein by reference in its entirety.

TECHNICAL FIELD

The following disclosure relates to a magnetic actuation system controlling a magnetic microrobot, a magnetic actuation catheter, or a guide wire by using a magnetic field, and more particularly, to a magnetic actuation system compatible with a C-arm that is applied to the C-arm, which is a mobile X-ray fluoroscopy device, in order to enable control of the microrobot or a catheter treatment in a human body by using the C-arm.

BACKGROUND

A microrobot or a catheter has been mainly developed as a means to effectively perform a medical task which is difficult for a human to directly perform, such as diagnosing a disease or delivering a drug by being inserted into a human body. An alternating magnetic field may be sometimes used to control the microrobot or the magnetic actuation catheter or a guide wire. In particular, a drilling motion using a rotating magnetic field of high magnetic density and high frequency may be sometimes used during a catheter treatment to open a clogged blood vessel in a blood vessel.

A three-dimensional magnetic actuation system has been conventionally disclosed in which a plurality of electromagnetic coils generating a magnetic field are attached to a three-dimensional supporter, a work space for actuating a magnetic robot is formed in the center of the supporter, each electromagnetic coil receives a current from the outside, and a three-dimensional magnetic field and a magnetic force are applied to the magnetic robot positioned in the workspace in a wireless manner, thereby controlling the magnetic robot. However, the magnetic actuation system described above may use eight electromagnetic coils radially arranged in the work space while being spaced apart from each other by a predetermined distance in order to apply the three-dimensional magnetic field and the magnetic force to the magnetic robot, thus having an external shape with a very large volume compared to the internal work space due to the plurality of coils, and consuming a lot of power to actuate the magnetic robot. In addition, the magnetic actuation system may have a sealed structure in which the plurality of electromagnetic coils are arranged outside the work space, and thus unable to be used with an medical imaging device such as a C-arm.

Therefore, there is a need to develop a magnetic actuation system that has a small volume and applicable to (or compatible with) the imaging device such as the C-arm to thus utilize image information using the C-arm during actuation of the magnetic robot, the magnetic actuation catheter, or the guide wire.

RELATED ART DOCUMENT

Patent Document

International Publication No. WO2018-030610 (published on Feb. 15, 2018)

SUMMARY

An embodiment of the present disclosure is directed to providing a magnetic actuation system compatible with a C-arm by being integrally provided with or separately combined with the C-arm.

Another embodiment of the present disclosure is directed to providing a magnetic actuation system which may actuate a robot, a magnetic actuation catheter, or a guide wire by applying a three-dimensional magnetic field and a magnetic force to the robot, the magnetic actuation catheter, or the guide wire regardless of an alignment direction of a C-arm.

Another embodiment of the present disclosure is directed to providing a magnetic actuation system which may control a three-dimensional movement of a robot with a minimum coil by combining an auxiliary coil and an electromagnetic coil with each other.

In one general aspect, provided is a magnetic actuation system compatible with a C-arm that is positioned on the C-arm including a C-shaped arc body, a receiver positioned at one end of the arc body, a transmitter positioned at the other end of the arc body, and a treatment space positioned between the receiver and the transmitter, the system including: an electromagnet unit including a combination of one or more electromagnets and positioned between the transmitter and treatment space of the C-arm; and a power supply unit supplying a current to the electromagnet unit, wherein the electromagnet unit is disposed below the treatment space by generating a magnetic field or a magnetic force through the current supplied from the power supply unit, and actuates a magnetic robot, a magnetic actuation catheter, or a guide wire, including a magnetic body, in the wireless manner.

The system may further include an auxiliary coil fixed to the receiver or transmitter of the C-arm and receiving the current from the power supply unit, wherein the auxiliary coil is disposed above the treatment space by generating the magnetic field or the magnetic force through the current supplied from the power supply unit, and actuates the magnetic robot, the magnetic actuation catheter, or the guide wire, including the magnetic body, in the wireless manner.

The auxiliary coils may be respectively positioned on the receiver and the transmitter.

The auxiliary coil may be positioned on the receiver or the transmitter, and have a shape corresponding to a shape of the receiver or that of the transmitter.

The auxiliary coil may have a circular, elliptical, or prismatic shape with a hollow part formed in a center of the auxiliary coil.

The electromagnet unit may be fixed to and supported by the arc body, and have a position changed in conjunction with a rotational motion of the arc body.

The electromagnet unit may be fixed to and supported by an external supporter positioned separately from the C-arm to be maintained to be fixed during a rotational motion of the arc body.

The auxiliary coil may be positioned on the receiver or the transmitter, and an X-ray generated from the transmitter may pass through a hollow part formed in a center of the auxiliary coil.

The electromagnet unit may control vectors of the magnetic robot, the magnetic actuation catheter, or the guide wire in three-dimensional directions (or X-axis, Y-axis, and Z-axis directions), and the auxiliary coil may control the vector in the vertical direction (or the Z-axis direction) to compensate for the magnetic field and magnetic force of the electromagnet unit in the vertical direction (or the Z-axis direction).

The electromagnet unit includes the plurality of electromagnets arranged radially based on a center of a plane while being spaced apart from each other by a predetermined distance to form an X-ray movement space in the center.

The electromagnet may have a central axis directed to a center of a plane, and is inclined toward the treatment space.

The electromagnet unit may include the four or more electromagnets radially arranged.

The magnetic actuation system may receive real-timeposition information of an actuation target through the C-arm and reflect the received information in controlling a position of the target.

BRIEF DESCRIPTION OF THE DRAWINGS

FIG. 1 is a perspective view of a C-arm using a magnetic actuation system according to an embodiment of the present disclosure.

FIG. 2 is a perspective view of the magnetic actuation system according to an embodiment of the present disclosure.

FIG. 3 is a perspective view of an embodiment showing the magnetic actuation system in which an electromagnet unit is fixed to and supported by an arc body.

FIG. 4 is a perspective view of an embodiment showing a magnetic actuation system in which the electromagnet is fixed to and supported by an external supporter.

FIG. 5 is a schematic view showing an arrangement relationship between the transmitter and receiver of the C-arm and an electromagnet in an embodiment showing the magnetic actuation system in which the electromagnet is fixed to and supported by the external supporter.

FIGS. 6A, 6B, and 6C are perspective views showing electromagnet units according to various embodiments of the present disclosure.

FIGS. 7A and 7B are perspective views of a rotation of a magnetic actuation system including the electromagnet unit using eight electromagnets, and FIG. 7C is a front view of the same.

FIG. 8A is a plan view of the electromagnet unit that shows a rotation of the magnetic actuation system including four electromagnets, and FIGS. 8B and 8C are perspective views of the same.

FIGS. 9A and 9B are comparison views comparing the rotation of the magnetic actuation system including the electromagnet unit using eight electromagnets (FIG. 9A) and the rotation of the magnetic actuation system including the electromagnet unit using four electromagnets (FIG. 9B).

FIG. 10 is a perspective view of an embodiment showing a magnetic actuation system having a pair of auxiliary coils.

FIGS. 11A and 11B are perspective views of a magnetic actuation system including a rectangular auxiliary coil.

FIGS. 12 and 13 are views each showing that a desired magnetic field may be generated regardless of a posture of the C-arm.

FIG. 14 is a view showing a strength of an output magnetic field relative to a current in each direction based on a rotation of the C-arm.

FIG. 15 is a flow chart showing a process in which position information of the robot obtained through the C-arm is used to generate the magnetic field and control the robot.

FIG. 16 is a view showing that the magnetic field is controlled when there is no position information of the robot.

FIG. 17 is a view showing that the magnetic field is controlled using the position information of the robot.

DETAILED DESCRIPTION OF EMBODIMENTS

Hereinafter, an embodiment of the present disclosure is described in detail with reference to the accompanying drawings.

FIG. 1 is an overall perspective view of a C-arm 1000 using a magnetic actuation system 100 according to an embodiment of the present disclosure. First, the description describes a basic configuration of the C-arm 1000 using the magnetic actuation system 100 according to an embodiment of the present disclosure that includes an arc 1100, a tray 1200, an actuation unit 1300, a manipulation unit 1400, and a body unit 1500.

The arc 1100 may have a C shape and may be rotated with respect to the tray 1200. The arc 1100 may include a C-shaped arc body 1110, a receiver 1120 positioned at one end of the arc body 1110, and a transmitter 1130 connected to the other end of the arc body 1110 and generating an X-ray.

The transmitter 1130 may include an X-ray generator generating the X-ray, and the X-ray may pass through a target positioned in a treatment space 2000 positioned between the transmitter 1130 and the receiver 1120, and then be transmitted to the receiver 1120.

The receiver 1120 may convert X-ray photons transmitted through the target into an image which may be recognized by human eyes.

The tray 1200 may connect the arc 1100 with the actuation unit 1300, and the actuation unit 1300 may implement the translational or rotational motion of the arc 1100 by using the tray 1200.

The manipulation unit 1400 may be used as a user interface, may transmit a signal to the transmitter or a control unit through a touch panel, or the like, and may confirm information detected by the receiver in a form of image information through a display.

The magnetic actuation system 100 according to an embodiment of the present disclosure may be compatible with the C-arm 1000 having the above configuration. Hereinafter, the magnetic actuation system 100 is described in detail.

FIG. 2 is a perspective view of the magnetic actuation system 100 according to an embodiment of the present disclosure.

A magnetic body may receive a magnetic torque aligned in a direction of a magnetic field, and the magnetic body may receive a magnetic force by which the magnetic body is moved to a position where a strength of the magnetic field is strong. Therefore, the torque and the force may be applied to the magnetic body in a wireless manner by controlling distribution of the magnetic field around the magnetic body. Accordingly, the magnetic actuation system 100 according to an embodiment of the present disclosure may control an end of a microrobot or that of a catheter in three dimensions by controlling the distribution of the magnetic field around the end of the microrobot or that of the catheter, including the magnetic body, and applying the torque and the force to the magnetic body in the wireless manner.

To this end, as shown in FIG. 2, the magnetic actuation system 100 may include an electromagnet unit 110 including a combination of a plurality of electromagnets 111 and an auxiliary coil 120. The electromagnet unit 110 may be positioned between the transmitter 1130 and treatment space 2000 of the C-arm 1000, and the auxiliary coil 120 may be positioned on the receiver 1120 of the C-arm 1000.

In addition, the electromagnet unit 110 may be fixed to and supported by the arc body 1110, and the electromagnet unit 110 in another embodiment may be fixed to and supported by an external supporter (not shown) positioned separately from the C-arm 1000.

The auxiliary coil 120 may be positioned on a side of the receiver 1120, and allow the X-ray to be transmitted to the receiver 1120 through a central hollow part. That is, the auxiliary coil 120 may be positioned not to prevent the receiver 1120 from receiving X-ray information.

In the magnetic actuation system 100 having the above configuration, each of the electromagnet 111 of the electromagnet unit 110 and auxiliary coil 120 may be connected to an independent power supply unit, and generate the three-dimensional magnetic field and magnetic force through a current supplied from the power supply unit to actuate a magnetic robot, a magnetic actuation catheter, or a guide wire in the wireless manner. In more detail, the electromagnet unit 110 may control vectors of the robot, the magnetic actuation catheter, or the guide wire in three-dimensional directions (or X-axis, Y-axis, and Z-axis directions), and the auxiliary coil 120 may additionally control a vector of the robot, the magnetic actuation catheter, or the guide wire in the vertical direction (or the Z-axis direction). The magnetic force generated in the Z-axis direction may be weak with only the electromagnet unit 110, and the magnetic force generated in the Z-axis direction may thus be compensated for through the auxiliary coil 120.

In addition, the magnetic actuation system 100 of the present disclosure may control the alignment and translational motion by applying the three-dimensional magnetic field and magnetic force to the robot, the magnetic actuation catheter, or the guide wire regardless of an alignment direction of the C-arm 1000.

In the electromagnet unit 110, the plurality of electromagnets 111 may be arranged radially based on the center of a plane while being spaced apart from each other by a predetermined distance to form an X-ray movement space in the center, and each electromagnet 111 may be inclined upward, i.e., toward the treatment space 2000 positioned above the electromagnet unit 110 to further secure the movement space and increase a rotation radius of the arc 1100. In addition, as the auxiliary coil 120 is disposed as described above, the insufficient strength (output) of the Z-axis magnetic field of the electromagnet unit 110 may be controlled by supplementing the strength (output) of the Z-axis magnetic field of the robot, the magnetic actuation catheter, or the guide wire by using the auxiliary coil 120.

FIG. 3 is a perspective view of an embodiment showing the magnetic actuation system 100 in which the electromagnet unit is fixed to and supported by the arc body.

As shown in the drawing, in the magnetic actuation system 100 of this embodiment, the electromagnet unit 110 may have a position changed in conjunction with the rotational motion of the arc 1100, thus preventing limitation in the rotation radius of the arc 1100 occurring due to the electromagnet unit 110. In addition, the electromagnet unit 110 may maintain the same output performance regardless of a posture of the arc 1100. The reason is that the limitation in the rotation radius of the arc 1100 may occur because an area where the X-ray is not transmitted due to the electromagnet unit 110 occurs when only the arc 1100 is rotated while the electromagnet unit 110 is fixed.

FIG. 4 is a perspective view of an embodiment showing a magnetic actuation system 200 in which an electromagnet unit is fixed to and supported by the external supporter.

As shown in the drawing, when an electromagnet unit 210 is fixed by the external support (not shown), the limitation may occur in the rotation radius of the arc 1100 because the electromagnet unit 210 is maintained to be fixed during the rotation of the arc 1100. However, the electromagnet unit 210 with a weight of about 300 Kg or more may be heavy, and thus be applied to a case where it is impossible to operate the system by fixing the electromagnet unit 210 to the arc 1100 and supporting the same.

In addition, the auxiliary coil 220 disposed above the treatment space 2000 may be moved in conjunction with the motion of the arc 1100 to have a changed position. However, the electromagnet unit 210 disposed below the treatment space 2000 may be fixed by the external supporter, and in this case, the electromagnet unit 210 may be fixed and disposed regardless of the motion of the arc 1100, thus always securing the treatment space 2000 for capturing the image that is positioned between the receiver and the transmitter regardless of the posture of the arc 1100. That is, it may be advantageous to secure the treatment space 2000 because the arrangement of the electromagnet units 210 is maintained to be fixed even when the arc 1100 is rotated.

FIG. 5 is a schematic view showing an arrangement relationship between the transmitter 1130 and receiver 1120 of the C-arm 1000 and an electromagnet 211 in an embodiment showing the magnetic actuation system 200 in which the electromagnet unit is fixed to and supported by the external supporter.

As shown in the drawing, each electromagnet 211 of the electromagnet unit 210 may be inclined with respect to a reference line L11 so that an angle $\theta1$ between the reference line L11 perpendicular to the ground and a direction L12 in which the magnetic field is generated is the same as the maximum angle $\theta2$ of the C-arm 1000 (that is, an angle between the reference line L11 perpendicular to the ground and a traveling direction L13 of the X-ray). The reason is to prevent interference between a trajectory of the X-ray of the C-arm 1000 and the electromagnet 211.

FIGS. 6A, 6B, and 6C are perspective views showing electromagnet units 110, 310, and 410 according to various embodiments of the present disclosure.

As shown in FIG. 6A, the electromagnet unit 110 is shown as including four electromagnets to efficiently generate the magnetic field or magnetic force for the three-dimensional actuation of the target, and may be implemented as long as the electromagnet unit 110 includes four or more electromagnets.

That is, an electromagnet unit 310 may include five electromagnets radially arranged as shown in FIG. 6B, or may include six electromagnets radially arranged as shown in FIG. 6C.

However, a space where the C-arm may be rotated may be increased when using fewer electromagnets, and the robot may be actuated with less power when using fewer electromagnets.

Therefore, in an embodiment, the present disclosure may control the alignment and translational motion of the magnetic robot with the electromagnet unit 110 including four electromagnets and one auxiliary coil 120, thus enabling the most efficient actuation structurally and electrically. That is, the present disclosure may be structurally efficient by having the internal treatment space 2000 that is larger compared to its external appearance, and may be electrically efficient by being actuated with less power.

FIGS. 7A and 7B are perspective views of a rotation of a magnetic actuation system 300 including the electromagnet unit using eight electromagnets, and FIG. 7C is a front view of the same; and FIG. 8A is a plan view of the electromagnet unit 110 that shows a rotation of the magnetic actuation system 100 including four electromagnets, and FIGS. 8B and 8C are perspective views of the same. In addition, FIGS. 9A and 9B are comparison views comparing the rotation of the magnetic actuation system including the electromagnet unit 310 using eight electromagnets (FIG. 9A) and the rotation of the magnetic actuation system including the electromagnet unit 110 using four electromagnets (FIG. 9B).

As shown in FIG. 7, a rotation angle of the arc 1100 may be limited due to the electromagnet unit 310 when many electromagnets 311 are positioned.

On the other hand, as shown in FIG. 8, it is possible to secure the space for the arc 1100 to be rotated in two axis directions (that is, the X-axis direction and the Y-axis direction) without limiting the angle when four electromagnets 111 are positioned.

Therefore, as shown in FIG. 9, the electromagnet unit including four electromagnets may utilize a wider space for the C-arm to be rotated compared to that electromagnet unit including five or more electromagnets.

FIG. 10 is a perspective view of an embodiment showing a magnetic actuation system 400 having a pair of auxiliary coils.

As shown in the drawing, auxiliary coils 421 and 422 may include the first auxiliary coil 421 positioned on the side of the receiver 1120 and the second auxiliary coil 422 positioned on a side of the transmitter 1130. In an embodiment described above, the magnetic field having a greater strength may be generated than when disposing one auxiliary coil.

FIGS. 11A and 11B are perspective views of a magnetic actuation system 500 including a rectangular auxiliary coil 520.

As shown in the drawing, a shape of the auxiliary coil 520 may correspond to a shape of the receiver 1120. Therefore, as shown in the drawing, when the receiver 1120 has a rectangular shape, the magnetic actuation system 500 may include the auxiliary coil 520 having the rectangular shape with a hollow inside.

In addition, the auxiliary coil may also be formed in a circular, elliptical, or polygonal shape based on a shape of the transmitter or that of the receiver.

Meanwhile, as shown in FIG. 4, the C-arm 1000 including the magnetic actuation system 500 in which the electromagnet unit 510 is fixed to and supported by the external supporter may generate the magnetic field in consideration of the relative arrangement of electromagnet units 510 that is changed based on the rotation angle of the arc 1100. That is, the C-arm 1000 including the magnetic actuation system 500 may control the magnetic field in consideration of the relative arrangement of the electromagnet units 510 based on the posture of the arc 1100.

The magnetic field of the magnetic actuation system 500 may be a linear combination of the magnetic fields of the respective electromagnets 211, and a change in the magnetic field based on the posture of the arc 1100 may be calculated through appropriate vector transformation and coordinate transformation.

That is, the magnetic field of the entire system may be represented as a sum of the magnetic field of the auxiliary coil 520 disposed above the treatment space 2000 and the magnetic field of the electromagnet unit 510 disposed below the treatment space 2000 as shown in Equation 1 below.

$$\overrightarrow{Bsystem} = \overrightarrow{Btop} + \overrightarrow{Bbottom} \qquad \text{(Equation 1)}$$

Here, the magnetic field generated by the entire system when the auxiliary coil 220 disposed above the treatment space 2000 is rotated in conjunction with the arc 1100 may be shown in Equation 2 below.

$$\overrightarrow{Bsystem} = \cdot R(\theta x, \cdot \theta y)\overrightarrow{(Btop)}\text{initial} + \overrightarrow{Bbottom} \qquad \text{(Equation 2)}$$

Here, $R(\theta x, \theta y)$ can be calculated through a rotation matrix (Equation 3) below.

$$\text{(Equation 3)}$$

$$R(\theta_x, \theta_y) =$$

$$R_y(\theta_y)R_x(\theta_x) = \begin{bmatrix} \cos\theta_y & \sin\theta_x \sin\theta_y & \cos\theta_x \sin\theta_y \\ 0 & \cos\theta_x & -\sin\theta_x \\ -\sin\theta_y & \sin\theta_x \cos\theta_y & \cos\theta_x \cos\theta_y \end{bmatrix}$$

(Btop)initial represents a vector of the magnetic field of the auxiliary coil when the arc 1100 has its initial posture.

FIGS. 12 and 13 are views each showing that a desired magnetic field may be generated regardless of a posture of the C-arm.

The desired magnetic field and magnetic force may be generated regardless of the posture of the C-arm when a current solution is calculated using Equations 1 to 3 to generate the desired magnetic field in consideration of the arrangement of the auxiliary coil 220 disposed above the treatment space 2000.

Each of FIGS. 12 and 13 shows an example in which the Z-axis magnetic field is output even in the C-arm having a different posture.

FIG. 14 is a view showing a strength of an output magnetic field relative to the current in each direction based on the rotation of the C-arm.

As shown in the drawing, the strength of the magnetic field that may be output in each direction may be changed based on the position of the auxiliary coil 220 disposed above the treatment space 2000, and the magnetic field of the maximum strength may be output toward the auxiliary coil 220 disposed above the treatment space 2000. That is, the system may control an arbitrary three-dimensional magnetic field regardless of the position of the auxiliary coil 220 disposed above the treatment space 2000.

In more detail, the system may have output performance (e.g., uniformity of the magnetic field or power consumption) changed based on the posture of the C-arm, and this change in the output performance may be calculated through Equations 1 to 3 above. Therefore, considering a movable range of the C-arm and a required magnetic field, the system may be designed to satisfy the required output regardless of the posture of the C-arm.

FIG. 14 shows that the output performance may be changed based the posture of the C-arm through the change in the output magnetic field relative to the current in each direction based on the posture of the C-arm, and the change in the performance may be calculated through Equations 1 to 3.

FIG. 15 is a flow chart showing a process in which position information of the robot obtained through the C-arm is used to generate the magnetic field and control the robot.

As shown in the drawing, the image information obtained through the C-arm 1000 may be used not only to perform the treatment, but also to obtain real-time position information of the magnetic robot, the magnetic actuation catheter, or the guide wire. Therefore, the magnetic actuation system 100 compatible with the C-arm of the present disclosure may always obtain the position information of the robot through the C-arm 1000, and thus generate the magnetic field and the magnetic force in consideration of the position, thereby generating the magnetic field and controlling the actuation of the robot more precisely than a magnetic actuation system operated separately from the C-arm.

In addition, the system 100 may control the motion of the robot by feedback using the real-time position information of the robot.

FIG. 16 is a view showing that the magnetic field is controlled when there is no position information of the robot, and FIG. 17 is a view showing that the magnetic field is controlled using the position information of the robot.

As shown in FIG. 16, the system may assume that the robot is positioned at the center of the system and apply the magnetic field when the position of the robot is not known. Therefore, an error in the magnetic field may be increased as the position of the actual robot is positioned far from the center of the system.

On the other hand, as shown in FIG. 17, the system may perform control for the desired magnetic field to be generated around the actual position of the robot, thus minimizing the error in the magnetic field when applying the magnetic field by using the position information obtained from the C-arm.

The magnetic actuation system 100 compatible with the C-arm according to an embodiment of the present disclosure having the above configuration may not only be electrically and structurally efficient by using fewer coils, but also be compatible with the C-arm which is a commonly used medical imaging device, thus enabling the magnetic robot, the magnetic actuation catheter, or the guide wire that are studied for various medical purposes to be used in an actual medical field.

As set forth above, the magnetic actuation system of the present disclosure having the above configuration may not only be electrically and structurally efficient by using fewer coils, but also be compatible with the C-arm which is a commonly used medical imaging device, thus enabling the magnetic robot or the magnetic actuation catheter that is studied for the various medical purposes to be used in the actual medical field.

In detail, the present disclosure may be efficiently actuated with less power by controlling the alignment and translational motion of the magnetic robot with five or more coils, and may be structurally efficient by having the internal work space larger compared to its external appearance.

In addition, the present disclosure may always secure the space for capturing the image that is positioned between the receiver and the transmitter regardless of the change in the position of the C-arm because the coil is moved together with the rotation of the C-arm, and may actuate the magnetic actuation catheter or the guide wire by applying the three-dimensional magnetic field and magnetic force to the robot, the magnetic actuation catheter, or the guide wire.

In addition, the present disclosure may control the magnetic field more precisely by not only utilizing the image information for the treatment through the C-arm but also obtaining the real-time position information of the magnetic robot, and by generating the magnetic field for actuating the robot always in consideration of the position of the robot.

The spirit of the present disclosure should not be limited to the embodiments described above. The present disclosure may be applied to various fields and may be variously modified by those skilled in the art without departing from the scope of the present disclosure claimed in the claims. Therefore, it is obvious to those skilled in the art that these alterations and modifications fall within the scope of the present disclosure.

What is claimed is:

1. A magnetic actuation system compatible with a C-arm that is positioned on the C-arm including a C-shaped arc body, a receiver positioned at one end of the arc body, a transmitter positioned at the other end of the arc body, and a treatment space positioned between the receiver and the transmitter, the system comprising:

an electromagnet unit including a combination of one or more electromagnets and positioned between the transmitter and treatment space of the C-arm; and a power supply unit supplying a current to the electromagnet unit, wherein the electromagnet unit is disposed below the treatment space by generating a magnetic field or a magnetic force through the current supplied from the power supply unit, and actuates a magnetic robot, a magnetic actuation catheter, or a guide wire, including a magnetic body wirelessly, wherein the electromagnet unit is fixed to and supported by an external supporter positioned separately from the C-arm, and wherein each electromagnet of the electromagnet unit is inclined at an inclination angle with respect to a reference line, which is perpendicular to a ground, such that the inclination angle is same as an angle between the reference line and a traveling direction of an X-ray transmitted from the transmitter.

2. The system of claim 1, further comprising an auxiliary coil fixed to the receiver or transmitter of the C-arm and receiving the current from the power supply unit, wherein the auxiliary coil is disposed above the treatment space by generating the magnetic field or the magnetic force through the current supplied from the power supply unit, and actuates the magnetic robot, the magnetic actuation catheter, or the guide wire, including the magnetic body wirelessly.

3. The system of claim 2, wherein the auxiliary coils are respectively positioned on the receiver and the transmitter.

4. The system of claim 2, wherein the auxiliary coil is positioned on the receiver or the transmitter, and has a shape corresponding to a shape of the receiver or a shape of the transmitter.

5. The system of claim 4, wherein the auxiliary coil has a circular, elliptical, or prismatic shape with a hollow part formed in a center of the auxiliary coil.

6. The system of claim 2, wherein the auxiliary coil is positioned on the receiver or the transmitter, and an X-ray generated from the transmitter passes through a hollow part formed in a center of the auxiliary coil.

7. The system of claim 2, wherein the electromagnet unit controls vectors of the magnetic robot, the magnetic actuation catheter, or the guide wire in three-dimensional directions (or X-axis, Y-axis, and Z-axis directions), and the auxiliary coil controls a vector in a vertical direction (or the Z-axis direction) to compensate for the magnetic field and magnetic force of the electromagnet unit in the vertical direction (or the Z-axis direction).

8. The system of claim 1, wherein the electromagnet unit includes a plurality of electromagnets arranged radially based on a center of a plane while being spaced apart from each other by a predetermined distance to form an X-ray movement space in the center.

9. The system of claim 1, wherein the electromagnet has a central axis directed to a center of a plane, and is inclined toward the treatment space.

10. The system of claim 1, wherein the electromagnet unit includes four or more electromagnets radially arranged.

11. The system of claim 1, wherein the magnetic actuation system receives real-time position information of an actuation target through the C-arm and reflects the received information in controlling a position of the target.

12. A magnetic actuation system compatible with a C-arm that is positioned on the C-arm including a C-shaped arc body, a receiver positioned at one end of the arc body, a transmitter positioned at the other end of the arc body, and a treatment space positioned between the receiver and the transmitter, the system comprising:

an electromagnet unit including a combination of one or more electromagnets and positioned between the transmitter and treatment space of the C-arm;

a power supply unit supplying a current to the electromagnet unit; and an auxiliary coil having a hollow portion in a center thereof and fixed to the receiver or transmitter of the C-arm and receiving the current from the power supply unit, wherein the electromagnet unit is disposed below the treatment space by generating a magnetic field or a magnetic force through the current supplied from the power supply unit, and actuates a magnetic robot, a magnetic actuation catheter, or a guide wire, including a magnetic body wirelessly, wherein the auxiliary coil is disposed above the treatment space by generating the magnetic field or the magnetic force through the current supplied from the power supply unit, and actuates the magnetic robot, the magnetic actuation catheter, or the guide wire, including the magnetic body wirelessly, and wherein an X-ray transmitted from transmitter passes through the hollow portion in the center of the auxiliary coil.

13. The system of claim 12, wherein the auxiliary coil has a shape corresponding to a shape of the receiver or a shape of the transmitter.

14. The system of claim 12, wherein the auxiliary coil has a circular, elliptical, or prismatic shape.

15. The system of claim 12, wherein the electromagnet unit is fixed to and supported by the arc body, and has a position changed in conjunction with a rotational motion of the arc body.

16. The system of claim 12, wherein the electromagnet unit is fixed to and supported by an external supporter positioned separately from the C-arm to be maintained to be fixed during a rotational motion of the arc body.

17. The system of claim 12, wherein the electromagnet unit controls vectors of the magnetic robot, the magnetic actuation catheter, or the guide wire in three-dimensional directions (or X-axis, Y-axis, and Z-axis directions), and the auxiliary coil controls a vector in a vertical direction (or the Z-axis direction) to compensate for the magnetic field and magnetic force of the electromagnet unit in the vertical direction (or the Z-axis direction).

18. The system of claim 12, wherein the electromagnet unit includes a plurality of electromagnets arranged radially based on a center of a plane while being spaced apart from each other by a predetermined distance to form an X-ray movement space in the center.

19. The system of claim 12, wherein the electromagnet has a central axis directed to a center of a plane, and is inclined toward the treatment space.

20. The system of claim 12, wherein the magnetic actuation system receives real-time position information of an actuation target through the C-arm and reflects the received information in controlling a position of the target.

* * * * *